United States Patent
Lützelschwab et al.

(10) Patent No.: US 11,460,397 B2
(45) Date of Patent: Oct. 4, 2022

(54) GAS MEASUREMENT SENSOR

(71) Applicant: CSEM Centre Suisse d'Electronique et de Microtechnique SA—Recherche et Développement, Neuchâtel (CH)

(72) Inventors: Markus Lützelschwab, Egolzwil (CH); Branislav Timotijevic, Lausanne (CH)

(73) Assignee: CSEM CENTRE SUISSE D'ELECTRONIQUE ET DE MICROTECHNIQUE SA, RECHERCHE ET DÉVELOPPEMENT, Neuchâtel (CH)

( * ) Notice: Subject to any disclaimer, the term of this patent is extended or adjusted under 35 U.S.C. 154(b) by 199 days.

(21) Appl. No.: 16/909,466

(22) Filed: Jun. 23, 2020

(65) Prior Publication Data
US 2020/0400556 A1 Dec. 24, 2020

(30) Foreign Application Priority Data

Jun. 24, 2019 (EP) .................................... 19181934

(51) Int. Cl.
*G01N 21/35* (2014.01)
*G01N 21/3504* (2014.01)
(Continued)

(52) U.S. Cl.
CPC ..... *G01N 21/3504* (2013.01); *G01N 21/0303* (2013.01); *G01N 33/0036* (2013.01)

(58) Field of Classification Search
CPC ........... G01N 21/3504; G01N 21/0303; G01N 33/0036
See application file for complete search history.

(56) References Cited

U.S. PATENT DOCUMENTS 5,414,264 A * 5/1995 Wong ................. G01N 21/0303
250/338.5
5,693,945 A * 12/1997 Akiyama ............... G01N 21/33
250/343

(Continued)

FOREIGN PATENT DOCUMENTS

EP 2538201 A1 12/2012

OTHER PUBLICATIONS

EP Search Report, dated Oct. 10, 2019, from corresponding EP application No. 19 18 1934.

*Primary Examiner* — Hugh Maupin
(74) *Attorney, Agent, or Firm* — Nixon & Vanderhye

(57) ABSTRACT

Gas measurement sensor including: a measurement chamber including an inlet and outlet for a gaseous sample to be measured; an infrared light source producing substantially collimated infrared light and to direct the infrared light into the measurement chamber; a beam splitter situated in the measurement chamber so as to receive the infrared light and to split the infrared light into a reference beam and a measurement beam such that the measurement beam has a longer pathway through the measurement chamber than the reference beam; a reference infrared detector arranged to receive the reference beam; and a measurement infrared detector arranged to receive the measurement beam. The beam splitter is arranged to reflect a first portion of the infrared light by specular reflection so as to form the reference beam, and to reflect a second portion of the infrared light by specular reflection so as to form the measurement beam.

15 Claims, 1 Drawing Sheet

(51) Int. Cl.
  *G01N 21/03* (2006.01)
  *G01N 33/00* (2006.01)

(56) References Cited

U.S. PATENT DOCUMENTS

| | | | |
|---|---|---|---|
| 6,512,230 B1* | 1/2003 | von Lerber | G01N 21/3504 |
| | | | 250/339.13 |
| 8,143,581 B2 | 3/2012 | Wong | |
| 8,217,355 B1 | 7/2012 | Wong | |
| 2011/0042570 A1* | 2/2011 | Wong | G01N 21/3504 |
| | | | 250/343 |
| 2011/0204236 A1 | 8/2011 | Wong | |
| 2012/0330568 A1 | 12/2012 | Izawa et al. | |

* cited by examiner

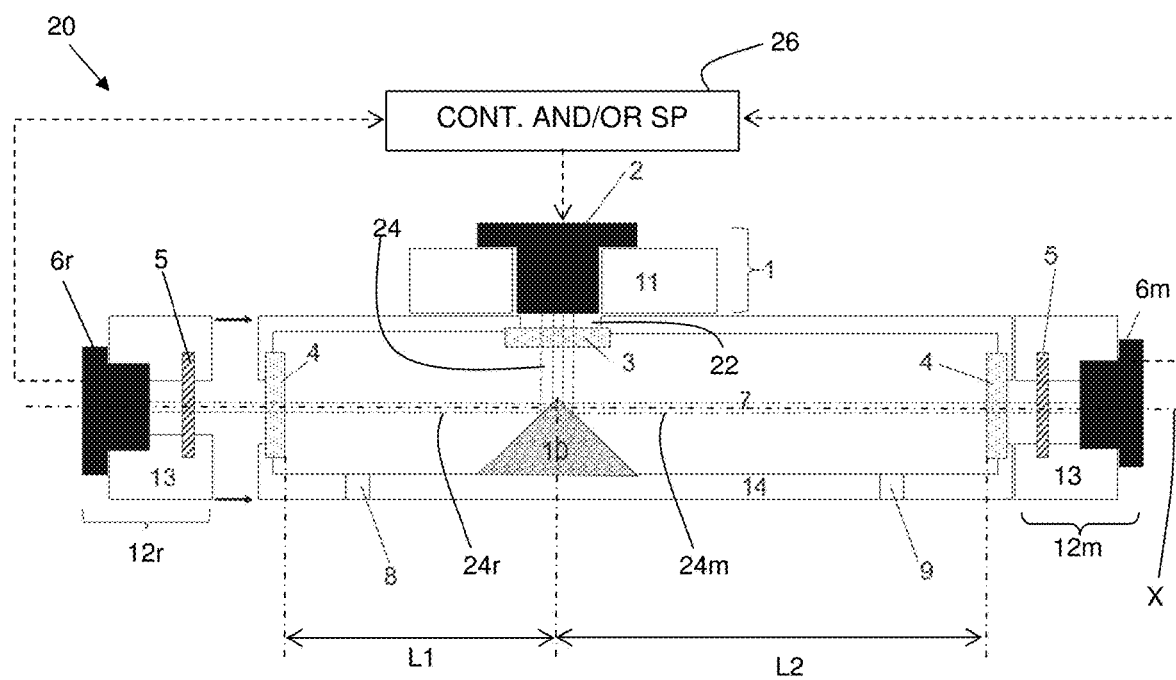

GAS MEASUREMENT SENSOR

TECHNICAL FIELD

The present invention relates to the technical field of gas measurement sensors. More particularly, it relates to an infrared gas measurement sensor exploiting absorption of infrared light by one or more gas specie(s) of interest so as to determine a concentration thereof.

STATE OF THE ART

U.S. Pat. Nos. 8,143,581 and 8,217,355 both disclose dual-beam non-dispersive infrared (NDIR) gas sensors, in which light from a single infrared (IR) source is directed along two parallel tubes which together form a measurement chamber. One of the tubes is longer than the other, and at the end of each is situated a corresponding IR sensor, adapted to receive infrared light. Each tube has a gas port situated near to its IR sensor, such that a gas to be tested can be made to flow through substantially the whole length of both tubes following a U-shaped path, with the result that the sample substantially fills the entire measurement chamber.

In this construction, the IR source is not collimated, and the wall between the two parallel tubes serves as a primitive form of beam splitter. Furthermore, waveguides are provided on the sidewalls of each tube so as to guide a maximum amount of IR light onto each sensor, appropriate IR filters being provided so as to isolate the absorption band of the specie of interest and to only pass this wavelength to the sensor.

The longer of the two tubes serves as a measurement pathway, and the shorter as a reference pathway. When no gas specie of interest (such as carbon dioxide, methane, a hydrocarbon, carbon monoxide, nitrous oxide or similar gas with a pronounced infrared absorption band corresponding to one or more wavelengths of IR light emitted by the IR source and receivable by the detectors) is present, the signal output by each IR sensor is substantially the same, within practical tolerances.

When a specie of interest is introduced into the measurement chamber, it absorbs a portion of the infrared light, causing the signal output by each IR sensor to drop. Since the measurement path is longer than the reference path, more IR light is absorbed therein, causing the IR sensor associated with this path to receive proportionally less IR light than the sensor associated with the reference path. The difference in, and/or the ratio of, the outputs of the two sensors can hence be exploited to measure not only the presence but also the concentration of the specie of interest present in the measurement chamber. This principle is well-known, and is described in detail in U.S. Pat. No. 8,143,581, herein incorporated by reference in its entirety.

However, this particular construction has several issues. Firstly, the use of the dividing wall between the two tubes so as to split non-collimated light makes it difficult to precisely control the proportion of the IR light directed along each tube, which affects the measurement accuracy. Furthermore, the use of waveguides on the sidewalls of the tubes is necessary to reduce transmission losses from light being absorbed by the sidewalls, which significantly complicates construction, increases the number of components and renders the sensor more expensive. In any case, significant IR energy is lost by this arrangement.

Furthermore, construction of the measurement chamber is complicated and requires specific manufacture.

An aim of the present invention is to at least partially overcome at least one of the above-mentioned drawbacks of the prior art.

DISCLOSURE OF THE INVENTION

More specifically, the invention relates to a gas measurement sensor as defined in claim 1. This sensor comprises:
- a measurement chamber comprising an inlet and an outlet for a gaseous sample to be measured;
- a source of substantially collimated infrared light, arranged to direct said infrared light into said measurement chamber. This source may be an incandescent bulb, an infrared LED, a MEMS IR source, an infrared laser or similar, and may be broadband or narrow band. It may be collimated by one or more lenses, masks or similar;
- a beam splitter situated in said measurement chamber so as to receive said infrared light and to split said infrared light into at least one reference beam and at least one measurement beam travelling along two different paths. The beam splitter is arranged in the measurement chamber such that the length of the pathway of the measurement beam through said chamber is longer than that of the reference beam through said chamber. The ratio of the length of these two pathways through the measurement chamber may, for instance, be between 1/5 and 4/5, preferably between 1/3 and 2/3;
- a reference infrared detector arranged to receive said reference beam;
- a measurement infrared detector arranged to receive said measurement beam, said measurement infrared detector typically being arranged at a greater distance from said beam splitter than said reference infrared detector as a result of the different path lengths as mentioned above.

According to the invention, said beam splitter is arranged to reflect a first portion of said infrared light impinging thereon by specular reflection so as to form said reference beam, and to reflect a second portion of said infrared light by specular reflection so as to form said measurement beam. To this end, the beam splitter may be for instance a prism or pyramid coated with a suitable infrared reflective substance such as gold, silver, titanium, aluminium or a dielectric material such as at least two, preferably at least four alternating layers of GaAs and $Al_xGa_{1-x}$ (i.e. at least one layer of each), with an appropriate degree of surface finish. More information regarding GaAs/$Al_xGa_{1-x}$ multilayers can be found in the paper "*High-performance near-and mid-infrared crystalline coatings*", Garrett D. Cole et al., Optica 3(6), March 2016.

By beam-splitting using specular reflection for splitting both portions of the incident IR light into the reference beam and the measurement beam, well-collimated beams can be produced with minimal losses, since there are no transmission or scattering losses as would be caused by e.g. using a partition wall as in the above-cited prior art, and which would also be caused when using a semi-silvered mirror, which is a common method of splitting a collimated beam. Indeed, it is possible that a maximum of the collimated light entering into the measurement chamber can be received by one or other of the detectors. Waveguides on the walls of the chamber are not necessary, and alignment of the measurement and reference beams is facilitated.

Advantageously, said reference beam and said measurement beam are substantially coaxial. This permits a simple, linear construction of the sensor.

Advantageously, at least one, and preferably both, of said infrared detectors is situated outside of said measurement chamber facing an infrared window provided in a wall of said measurement chamber.

Advantageously, at least one, preferably both, of said infrared detectors is removably mounted to said measurement chamber at the exterior thereof. This enables easy replacement of broken detectors, exchange of detectors optimised to detect a particular gas species, or similar. Further advantageously, said at least one infrared detector is fixed to a corresponding holder, said holder also supporting an infrared filter arranged such that said infrared filter is disposed between said infrared detector and said measurement chamber when said holder is mounted to said measurement chamber. This enables easy exchange of not only the detector, but also the filter in the case in which this latter is removably mounted on the holder.

Advantageously, said measurement chamber is situated in the interior of a tube, the tube hence delimiting the outer walls of the chamber. Tubes, whether of circular, oval or polygonal cross section, are simple to produce, particularly when they are substantially straight, i.e. substantially rectilinear.

A particularly advantageous construction is one in which the infrared light source is fixed to the inside or the outside of a sidewall of said tube, each of said infrared detectors being fixed to a respective end of said tube. This construction is simple and compact, and infrared transmissive windows can be provided on or in the sidewall and end faces of said tube if required.

Advantageously, said prism or pyramid is coated with at least one of gold, aluminium, silver, titanium, a dielectric material.

Advantageously, at least one of said gas inlet and said gas outlet is covered by a permeable membrane to prevent ingress of dust and other contaminants. In the case in which the permeable membrane is selective for one or more gas species of interest, it can help to concentrate said species in the measurement chamber.

The above-mentioned features can be combined in any manner which makes technical sense.

BRIEF DESCRIPTION OF THE DRAWINGS

Further details of the invention will appear more clearly upon reading the description below, in connection with the following FIGURE which illustrates:

FIG. 1: a schematic cross-sectional view of a nonlimiting embodiment of a gas sensor according to the invention.

EMBODIMENTS OF THE INVENTION

FIG. 1 illustrates schematically a gas measurement sensor 20 according to the invention.

This sensor 20 comprises a measurement chamber 7 situated inside a tube 14, which may be of cylindrical or prismatic form, and extends along a longitudinal axis X. The dimensions of the tube are not critical, and as a rough guide approximate dimensions of 70-100 mm×8-20 mm×8-20 mm would be typical. In the sidewalls of the tube 14, proximate to each of its extremities, is a corresponding gas port 8, 9, each serving either as a gas inlet or gas outlet, through which a sample can be introduced into and exhausted from the measurement chamber 7. Gas conduits can be attached to one or both ports 8, 9, a pressure differential generated between them causing the gas sample to flow through the chamber 7 as is generally known, and either or both of the ports 8, 9 may be provided with a permeating membrane (not illustrated) which may or may not be selective for the gas specie(s) of interest.

Mounted on or adjacent to a sidewall of this tube 14 is an infrared (IR) source module 1, comprising a collimated infrared source 2 mounted to a holder 11. The IR source may be e.g. an incandescent bulb, a MEMS IR source, an LED or similar, and may be operated by a controller 26 (as illustrated by the dashed arrow), or may simply have its own standalone power supply. The IR source 2 may be continuous or pulsed, and may be collimated by means of masks and/or lenses, or may indeed be an infrared laser.

IR source 2 may be narrow band or broad band, emitting in the wavelength range of 1 µm to 11 µm, more typically in the range of 2 µm to 6 µm or to 8 µm, even more typically 3 µm to 4 µm, depending on the specie or species of interest. This specie or species may for instance be one or more of CO, $CO_2$, $N_2O$, $NO_2$, $H_2O$, $CH_4$, any other hydrocarbons, $SO_2$, $SO_3$, explosive gases, refrigerants such as R12, R22, R32, R134a, R410 or similar, anaesthetic gases or similar gases with absorption bands in the infrared range.

The holder can be fixed to the tube 14 by any convenient means, such as gluing, welding, or by being integrally formed therewith. Alternatively, it can be removably mounted, for instance by being dovetailed, bayonet-mounted, screwed or threaded thereupon. The tube 14 is typically opaque to infrared and visible wavelengths in order to exclude undesired wavelengths of light from entering thereinto and negatively affecting the measurements.

An opening 22 is provided in the sidewall of the tube 14 to allow the collimated IR radiation 24 to enter, an infrared window 3 being provided so as to seal the opening 22. As illustrated, this window 3 is fixed on the inside of the sidewall, however it can be flush-fitted thereto, or even be provided on the outside of the sidewall. This window 3 may permit a range of IR wavelengths to pass into the measurement chamber 7, or may be selective, only allowing through the wavelengths corresponding to one or more of the absorption bands of the specie(s) of interest. Suitable materials for the window 2 are, for instance, sapphire, silicon, zinc selenide, zinc sulphide, calcium fluoride, magnesium fluoride, sodium chloride and potassium bromide, and an anti-reflective coating can be provided thereupon if desired. In the case in which the IR source module 1 is sealingly mounted to the tube 14, the window 3 can be omitted.

A beam splitter 10 is provided inside the measurement chamber 10, mounted on the sidewall of the tube such that it faces the opening 22, in order to split the incident IR radiation 24 into a reference beam 24r, passing to the left on the FIGURE, and a measurement beam 24m, passing to the right.

According to the invention, this beam splitter 10 works by specular reflection. To this end, in the illustrated embodiment the beam splitter 10 is a prism with a 90° apex angle, the prism being coated in an infrared-reflecting layer such as gold, aluminium, silver, titanium, a dielectric material at least two, preferably at least four alternating layers of GaAs and $Al_xGa_{1-x}$ or similar and being positioned such that each of its faces makes substantially the same angle with the incident IR light 24, specifically 45° in the illustrated embodiment. In other words, a plane which bisects the planes of the two faces of the prism is substantially aligned with the direction of incident IR light. As a result, since the incident IR light is aligned with the apex of the prism and has a finite beam width with a predetermined diameter, a portion of the incident IR light 24 falling on one face of the prism is redirected so as to become the reference beam 24r, a portion falling on the other face being redirected in a different direction so as to become the measurement beam 24m. The diameter and intensity of the incident IR light beam can be tuned if required.

Since the incident IR beam 24 is split by specular reflection, its attenuation is minimised, which is a drawback of beam splitting by other methods such as semi-silvered mirrors, in which the beam is split by a portion thereof being reflected, the other portion thereof being transmitted therethrough. This can lead to absorption by the material of the mirror, unwanted interference effects, and so on, these issues being completely avoided by the use of specular reflection alone.

This arrangement also permits simple optimisation of the diameter of the reference beam 24r and the measurement beam 24m, each of which retain their collimation.

At each end of the tube 14 is an infrared window 4, similar to infrared window 3, and in respect of which the same considerations apply, and is optional in the case in which the detector modules 12r, 12m are sealingly mounted to the chamber. Facing each infrared window 4 is an infrared detection module 12r, 12m, which advantageously can be removably mounted, as illustrated schematically with reference to the left-hand (reference) module 12r. The modules 12r, 12m can be fixed e.g. by screws, a dovetail fitting, a bayonet fitting, or any other convenient means.

Each of these modules comprises a holder 13 supporting an IR detector 6r, 6m, and an infrared filter 15 (such as Fabry Perot filters) arranged perpendicular to the direction of impinging IR light (i.e. perpendicular to the longitudinal axis X in the illustrated construction), the pass-band of the infrared filter is adapted to the absorption bands of the specie(s) of interest, in order to exclude unwanted wavelengths and hence to improve the signal to noise ratio. IR sensors 6r, 6m are operatively connected (as indicated by means of dashed arrows) to suitable signal processing (SP) electronics e.g. provided in controller 26 or in a standalone processing unit as is generally known. This signal processing per se is known to the skilled person and hence need not be discussed in detail.

It should be noted that the IR detectors 12 and the IR filters 5 can be fixed directly to the tube 14, and do not have to be provided in a detachable module, and that the IR windows 4 may also act as IR filters. However, the use of removable IR detection modules 12r, 12m permits simple exchange of modules 12r, 12m in order to replace failed ones, or to adapt the sensor to detect different gases in the case in which different modules 12 with different filters 5 and/or different detectors 6r, 6m are provided. Furthermore, the filters 5 can be removably mounted on the corresponding holder 13. In any case, the detectors 6r, 6m are typically thermal sensors such as thermocouples, photodetectors, infrared photodiodes, or similar.

As can clearly be seen in FIG. 1, the IR source 2 and the beam splitter 10 are not arranged equidistant from each end of the tube 14. Indeed, the distance L1 between the apex of the beam splitter 10 and the IR window 4 at the reference (left-hand)) end of the tube 14 is shorter than the distance L2 between said apex and the IR window 4 at the measurement (right-hand) end of the tube 14. The ratio L1/L2 is typically between 4/5 and 1/5, preferably between 1/3 and 2/3.

Since L1 is shorter than L2, the absorption pathway through the gas within the chamber 7 is shorter from the beam splitter 10 to the left-hand IR detector 6r than to the right-hand IR detector 6m. As a result, when a specie of interest is present in the chamber 7, more IR light is absorbed in the right-hand pathway 24m than in the left-hand pathway 24r. This difference and/or ratio is measured by the IR detectors 6r, 6m, and can be exploited by signal processing hardware and/or software as is generally known in order to determine the concentration of said specie of interest in the sample chamber 7.

The position of the beam splitter 10 with respect to the collimated IR source 2 can be varied by means of a suitable mechanism in order to modify the proportion of IR radiation being split in each direction parallel to the longitudinal axis X by moving the beam splitter 10 parallel to this axis. Typically, this proportion is 50% towards the reference side and 50% towards the detection side, but other splits are possible. The alignment of the measurement beam 24m and reference beam 24 can also be adjusted by pivoting the beam splitter 10 about one or more appropriate axes. As a result, the "zero point" of the sensor can be precisely set for each individual system, improving measurement accuracy.

It should be noted that the construction of FIG. 1 is not to be construed as limiting. It is possible, for instance, for the tube 14 to be bent into a "V" shape rather than straight, the apex angle of the beam splitter 10 being adapted in consequence so as to account for the angle of the "V".

Furthermore, it is also possible to apply the same principle to a sensor having more than one reference and/or measurement pathway. To this end, the tube 14 may be branched such that it comprises three, four or even more sections each leading to a respective IR detector 6r, 6m facing the beam splitter 10, the lengths of the various measurement pathways being the same or different, and likewise the lengths of the various reference pathways being the same or different.

In order to split the IR beam 24 in more than two directions, the beam splitter 10 can be constructed as a pyramid rather than as a prism, the pyramid comprising the corresponding number of sides (i.e. three, four or more) such that light can be directed towards each IR detector 6r, 6m. In an alternative construction, the measurement chamber can be cylindrical or prismatic of low aspect ratio (i.e. the height being less than the width), the detectors 6r, 6m being provided fixed to the outer wall of this structure, the IR source 2 being decentred with respect thereto so as to provide the different path lengths as mentioned above.

In any case, further variations to the invention are not excluded, the scope of the invention being as defined in the appended claims.

The invention claimed is:

1. A gas measurement sensor comprising:
a measurement chamber comprising an inlet and an outlet for a gaseous sample to be measured;
an infrared light source configured to produce substantially collimated infrared light and to direct said infrared light into said measurement chamber;
a beam splitter disposed in said measurement chamber to receive said infrared light and to split said infrared light into a reference beam and a measurement beam such that said measurement beam has a longer pathway through said measurement chamber than a pathway of said reference beam;
a reference infrared detector configured to receive said reference beam; and
a measurement infrared detector configured to receive said measurement beam;
wherein said beam splitter is configured to reflect a first portion of said infrared light by specular reflection to form said reference beam, and to reflect a second portion of said infrared light by specular reflection so as to form said measurement beam.

2. The gas measurement sensor according to claim 1, wherein said beam splitter is a prism which is infrared reflective in at least a zone of a surface configured to receive said infrared light, and an apex of said prism faces said infrared light source.

3. The gas measurement sensor according to claim 2, wherein said prism is coated with at least one of gold, aluminium, silver, titanium, and a dielectric material.

4. The gas measurement sensor of claim 3, wherein said prism is coated with the dielectric material in the form of a plurality of alternating GaAs and $Al_xGa_{1-x}$ layers.

5. The gas measurement sensor according claim 1, arranged such that said reference beam and said measurement beam are substantially coaxial.

6. The gas measurement sensor according claim 1, wherein at least one of said infrared detectors is disposed outside of said measurement chamber facing an infrared window provided in a wall of said measurement chamber.

7. The gas measurement sensor according to claim 1, wherein at least one of said infrared detectors is removably mounted to said measurement chamber at the exterior thereof.

8. The gas measurement sensor according to claim 7, wherein said at least one infrared detector is fixed to a corresponding holder, said holder supporting an infrared filter such that said infrared filter is disposed between said infrared detector and said measurement chamber when said holder is mounted to said measurement chamber.

9. The gas measurement sensor according to claim 1, wherein said measurement chamber is disposed in the interior of a tube.

10. The gas measurement sensor according to claim 9, wherein said tube is substantially straight.

11. The gas measurement sensor according to claim 10, wherein said infrared light source is fixed to a sidewall of said tube, each of said infrared detectors being fixed to a respective end of said tube.

12. The gas according to claim 1, wherein at least one of said gas inlet and said gas outlet is covered by a permeable membrane.

13. The gas measurement sensor according to claim 1, wherein said beam splitter is a pyramid which is infrared reflective in at least a zone of a surface configured to receive said infrared light, and an apex of said pyramid faces said infrared light source.

14. The gas measurement sensor according to claim 13, wherein said pyramid is coated with at least one of gold, aluminium, silver, titanium, and a dielectric material.

15. The gas measurement sensor of claim 13, wherein said pyramid is coated with the dielectric material in the form of a plurality of alternating GaAs and $Al_xGa_{1-x}$ layers.

* * * * *